United States Patent
Jakubowska-Zahorska et al.

(10) Patent No.: US 9,850,467 B2
(45) Date of Patent: Dec. 26, 2017

(54) METHODS OF USING T4 BACTERIOPHAGE IN TREATMENT OF ADENOVIRAL INFECTIONS CAUSED BY HADV-5

(71) Applicants: Warszawski Uniwersytet Medyczny, Warsaw (PL); Instytut Immunologii I Terapii Doswiadczalnej im. Ludwika Hirszfelda PAN we Wroclawiu, Wroclaw (PL)

(72) Inventors: Renata Jakubowska-Zahorska, Warsaw (PL); Maciej Przybylski, Warsaw (PL); Jan Borysowski, Warsaw (PL); Andrzej Gorski, Warsaw (PL); Beata Weber-Dabrowska, Wroclaw (PL)

(73) Assignees: Warszawski Uniwersytet Medyczny, Warsaw (PL); Instytut Immunologii i Terapii Doswiadczalnej im. Ludwika Hirszfelda PAN we Wroclawiu, Wroclaw (PL)

( * ) Notice: Subject to any disclaimer, the term of this patent is extended or adjusted under 35 U.S.C. 154(b) by 0 days.

(21) Appl. No.: 14/895,541

(22) PCT Filed: Jun. 3, 2014

(86) PCT No.: PCT/IB2014/061922
§ 371 (c)(1),
(2) Date: Dec. 3, 2015

(87) PCT Pub. No.: WO2014/195871
PCT Pub. Date: Dec. 11, 2014

(65) Prior Publication Data
US 2016/0122725 A1    May 5, 2016

(30) Foreign Application Priority Data
Jun. 3, 2013 (PL) .......................... 404176

(51) Int. Cl.
*C12N 7/00* (2006.01)
*A61K 35/76* (2015.01)

(52) U.S. Cl.
CPC ................ *C12N 7/00* (2013.01); *A61K 35/76* (2013.01); *C12N 2795/10132* (2013.01)

(58) Field of Classification Search
None
See application file for complete search history.

(56) References Cited

U.S. PATENT DOCUMENTS

2012/0122186 A1   5/2012   Weber-Dabrowska et al.

FOREIGN PATENT DOCUMENTS

| JP | 2007204415 A | 8/2007 |
| WO | 03000274 A2 | 1/2003 |
| WO | 2004013317 A1 | 2/2004 |

OTHER PUBLICATIONS

Denou et al,. Virology, 2009, 388:21-30.*
Bruttin et al., Antimicrobial Agents and Chemotherapy, Jul. 2005, 49(7):2874-2878.*
Gaggar et al., Nature Medicine, Nov. 2003, 9(11):1408-1412.*
XP-002728755—Database WPI (Week 201280); Thomson Scientific, Londong, AN2012-L11827, (2012).

* cited by examiner

*Primary Examiner* — Nicole Kinsey White
(74) *Attorney, Agent, or Firm* — Fox Rothschild LLP

(57) ABSTRACT

We disclose the use of a strain of bacteriophages in the manufacturing of a preparation for improving the state of health of patients infected with adenoviruses, wherein preferably the preparation produced is used for the treatment or prevention of adenoviral infections, particularly those caused by HAdV, preferably HAdV-5.

3 Claims, 1 Drawing Sheet

METHODS OF USING T4 BACTERIOPHAGE IN TREATMENT OF ADENOVIRAL INFECTIONS CAUSED BY HADV-5

CROSS-REFERENCE TO RELATED APPLICATION

This application is a U.S. National Phase of International Application No. PCT/IB2014/061922, filed Jun. 3, 2014, which claims priority to Poland Application No. P.404176, filed Jun. 3, 2013, the disclosures of which are incorporated herein by reference.

The subject of the present invention is a novel use of bacteriophages in medicine. In particular, the present invention relates to a novel use of bacteriophages in the manufacturing of preparations designed for the prevention or treatment of infections caused by disease-causing viruses in humans.

There are known adenoviruses of the C species (in particular type 5), which are responsible for infections in humans, which particularly relate to the respiratory tract. There are also bacterial viruses known, in particular the T4 phage.

Despite the progress in biomedical science, there is a constant need for novel drugs capable of treating diseases caused by viruses, in particular adenoviruses.

Unexpectedly, such a defined goal has been attained in the present invention.

The subject of the present invention is the use of a strain of bacteriophages in the manufacturing of a preparation for improving the state of health of patients infected by adenoviruses, wherein preferably the manufactured preparation is used for the treatment or prevention of adenovirus infections, particularly those caused by HAdV, preferably HAdV-5. Preferably, the bacteriophage strain used is the T4 phage or derivatives thereof.

Bacteriophages used according to the present invention should be devoid of deleterious contaminants, such as bacterial endotoxins. Appropriate bacterial strains may be obtained, for example, using methods described in the Polish patent applications by the Institute of Immunology and Experimental Therapy of the Polish Academy of Sciences in Wroclaw: P.348740 from Jul. 18, 2001, P 354822 from Jun. 30, 2002, P.355355 from Aug. 5, 2002, or the international application PCT/PL02/000053 dated Jul. 18, 2002.

Unexpectedly, it turned out that bacteriophage preparations, in addition to antibacterial properties are non-toxic to human cells and exhibit activity against adenoviruses. In particular, they decrease the infectious activity of HAdV adenoviruses against human cells and they decrease the level of intracellular replication of adenoviruses.

Unexpectedly, it turns out (as shown by the results below) that bacteriophages, particularly the T4 phage or derivatives thereof, may be successfully used for the treatment or prevention of adenoviral infections, particularly those caused by HAdV.

In particular T4 phage derivatives that can be used according to the present invention should be understood to be a bacteriophage strain which possesses in one of its surface proteins, particularly the p24 protein, the KGD (Lys-Gly-Asp) domain, thanks to which it can bind the CD51/CD61 cell receptor, meaning integrins of the ITGAV family ($\alpha v \beta 3$, $\alpha v \beta 5$). Such bacteriophages strains may be contained using isolation from natural sources as well as commonly accessible molecular biology methods.

Because human adenoviruses (HAdV) are adsorbed onto the surface of cells via the CAR receptor, whereas the receptors responsible for virus entry into the cells are the integrins $\alpha v \beta 3$ and $\alpha v \beta 5$, the authors postulate that by blocking the surface receptor for HAdV, bacteriophages can inhibit the penetration, and thereby the proliferation of adenoviruses in cell cultures.

To summarise, the present invention opens novel perspectives for the medicinal use of bacteriophages, including in anti-adenovirus therapy.

The description of the present invention has been supplemented with the following Figures.

Figure 1:
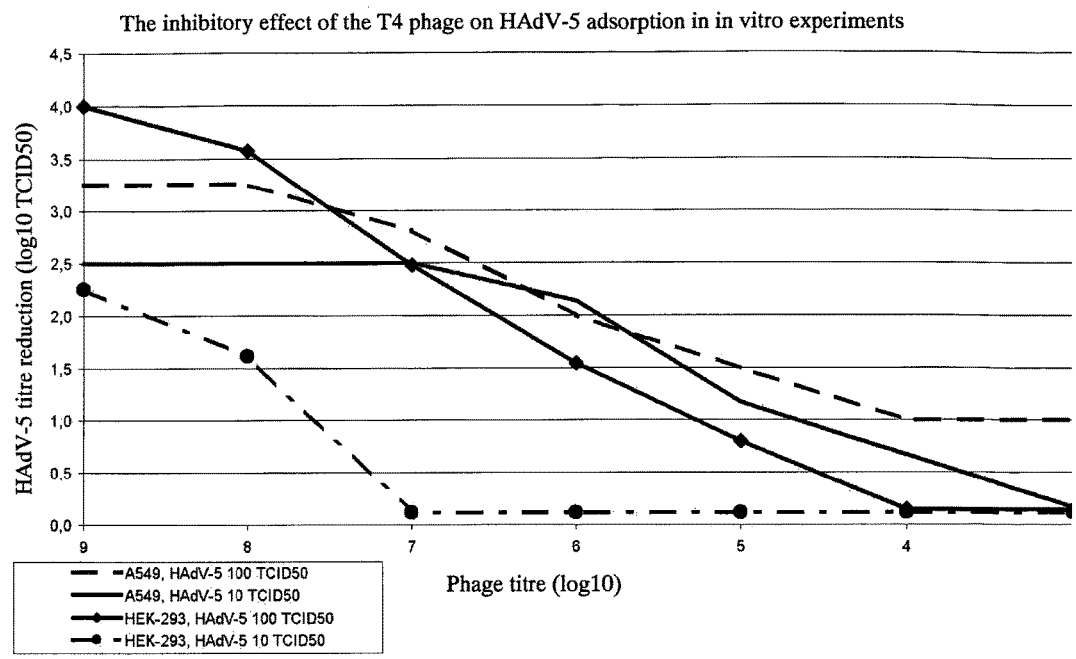
FIG. 1 shows the inhibitory effect of preparations containing the T4 phage on HAdV-5 adsorption.

To better understand the nature of the present invention, it has been illustrated with the following examples. It would be erroneous, however, to limit the scope of the present invention solely to these example embodiments.

Example 1. The Effect of the T4 Phage on HAdV-5 Activity Against Human Cells

In the first stage, we evaluated the effect of preincubating cell lines with a T4 phage suspension on the replication ability of adenoviruses of the C species (type 5), responsible for respiratory tract infections (evaluation of the effect of phages on the adsorption stage of HAdV).

In the next stage, we evaluated the effect of the T4 phage on HAdV-5 replication with the simultaneous inoculation of the cell culture with the phage and adenoviruses (evaluation of the effect of the phage on HAdV replication).

For the experiments we selected two types of cell lines: (i) a cell line incapable of producing interferon (A549, continuous tumour line derived from a laryngeal epithelioma) and (ii) a cell line capable of synthesizing interferon (HEK-293, transfected human embryonic line derived from the kidney epithelium). Both lines are fully susceptible to adenovirus infections.

The evaluation of the effect of the T4 phage on the infectious activity of adenoviruses species C in cells of the immortalised line A549 and the diploid human HEK-293 cell line.

1. Materials

A. Cell cultures:
Immortalised line $A_{549}$ (human laryngeal tumour line, ATCC-CCL-185)
Diploid line HEK-293 (human embryonic cell line transformed with type 5 adenoviruses, ATCC-CRL-1573)
B. Virus: Human adenoviruses (HAdV), species C, type 5, ATCC VR-5 (causing upper respiratory tract infections).
C. T4 bacteriophage (*E. coli*), obtained at the Institute of Immunology and Experimental Therapy of the Polish Academy of Sciences in Wroclaw. Bacteriophage titre: $2 \times 10^{10}$, lipopolysaccharide (LPS) content in the phage preparation: 163.5 EU/ml.
D. LPS control preparation containing 13.0 EU/ml lipopolysaccharide.

2. Methodology

A. Cell production
a. Immortalised line $A_{549}$. The cells were passaged continuously in Eagle's medium with 10% calf foetal serum and antibiotics.

b. Diploid line HEK-293. The cells were passaged continuously in Dulbecco medium with 10% calf foetal serum and antibiotics.

After obtaining the initial populations, we proliferated the cells in quantities necessary for the experiment and banked them in Eagle's medium ($A_{549}$) or Dulbecco medium (HEK-293), with 10% calf foetal serum and 10% dimethylsulphoxide at a temperature of −70° C. The aforementioned cell cultures constituted a substrate for proliferating and titrating HAdV-5 VR-5 and evaluating the antiviral activity of the T4 phage.

B. The proliferation of HAdV-5 was performed in both the aforementioned cell lines. The cultures were infected with viral suspensions containing 1 $TCID_{50}$/cell (tissue culture infective dose). Virus harvesting was performed after achieving 100% cytopathy characteristic of HAdV. Intracellular virions were released using freeze-thaw cycles, and the resulting post-centrifugation supernatant was aliquotted into ampoules and stored at a temperature of −70° C. Virus pools obtained from both cell lines were tested each time for infective activity.

C. Evaluation of the HAdV-5 infectious activity. The infectious activity of adenoviruses was evaluated in mature, 24-hour cultures of $A_{549}$ and HEK-293 cells. After 60 minutes of incubating the virus with cells at a temperature of 37° C., the cultures were rinsed with a PBS solution, and the infected cells were supplemented with Eagle's or Dulbecco maintenance medium depending on the cell line, with an addition of 2% foetal calf serum and antibiotics. The virus titre was evaluated after 48 hours of incubation at a temperature of 37° C. based on the microscopic evaluation of the cytopathic effect (CPE). The infective virus titre was calculated using the Reed-Munch method and expressed in terms of base 10 logs of $TCID_{50}$. The HAdV-5 infective activity was evaluated each time for each phage preparation experiment.

D. Preparing the phage preparation. The obtained phage preparation was diluted such that we obtained a preparation containing LPS at a concentration equal to that of the control LPS preparation (13.0 EU/ml). This preparation, containing the T4 phage at a titre of $1.47 \times 10^9$, was used in subsequent experiments.

E. Cytotoxicity determination of the phage preparation and control LPS preparation. The microscope cytotoxicity evaluation was performed based on cell morphology in terms of the cytopathic effect after a 48-hour incubation of $A_{549}$ and HEK-293 cells at a temperature of 37° C., in the presence of the T4 phage suspension at a titre of $1.47 \times 10^9$, containing 13.0 EU/ml LPS or the control preparation containing 13.0 EU/ml LPS. Both preparations were, diluted tenfold to $1 \times 10^{-7}$; Preparations used in the A549 experiments were diluted with Eagle's medium containing 2% foetal calf serum, whereas in HEK-293 experiments we used Dulbecco medium containing 2% foetal calf serum.

F. The evaluation of the effect of phages on the adsorption phase of adenoviruses was based on the introduction of the T4 phage at a titre of $1.47 \times 10^9$ to $1.47 \times 10^3$ PFU/ml into mature cell cultures of both types for 2 hours of incubation at a temperature of 37° C. Next, after the phage was rinsed off, the cultures were infected with a suspension of HAdV-5 at doses of 10 and 100 $TCID_{50}$/ml for an hour at a temperature of 37° C. After rinsing again the cultures were incubated for 48 hours at 37° C., and then the intracellular virions were freed using the freeze-thaw method on infected cultures. The resulting virus suspensions were titrated using the Reed-Munch method and compared to the control virus.

G. The effect of the phage on the replication phase of intracellular HAdV-5 was also evaluated using on both the abovementioned cell types and was based on the infection of both types of cultures with an adenovirus suspension, as shown above, with a one hour incubation at a temperature of 37° C. Next, after rinsing off the adenoviruses, we supplemented appropriate cultures with T4 phage titres analogous to those in point 5. The cultures were incubated for 48 hours at a temperature of 37° C. The intracellular virions and HAdV-5 titre determination were performed as in point F.

H. In the end stage, we determined the T4 phage inhibitory activity via the HAdV-5 tire reduction method. We collected all samples, both from experiments evaluating the effect of the phage on the adsorption phase, and the replication of adenoviruses. After releasing the intracellular virions, we evaluated the infectious activity of the virus in appropriate cell cultures, making serial dilutions ($1 \times 10^{-1}$ do $1 \times 10^{-8}$) of all samples. The virus titre was determined based on the occurrence of the cytopathic effect (CPE). The antiviral activity of the evaluated T4 phage was determined based on titre reduction in relation to the control virus used to infect the cultures without an addition of the T4 phage. these values were expressed in terms of the $TCID_{50}$ of HAdV-5 VR5. Values obtained from three consecutive experiments for each cell line were defined in terms of $ID_{50}$, a unit indicating HAdV-5 titre reduction caused by the T4 phage.

3. Results

A. Evaluation of the cytotoxicity of the phage preparation and control LPS preparation. After a 48-hour incubation of $A_{549}$ and HEK-293 cells, in both cell lines we observed no cytotoxic effect, in the full range of phage preparation dilutions, nor in the control LPS preparation.

B. Evaluation of T4 bacteriophages on the adsorption phase of adenoviruses of the C species (HAdV-5)—FIG. 1

B.1 HAdV-5 at a titre of 100 $TCID_{50}$, A549 line, averaged results of 12 determinations.

| T4 bacteriophage titre | Control HDaV-5 titre | HDaV-5 titre in lines treated with the T4 phage | HDaV-5 titre reduction in relation to the control[log10 of the titre] |
|---|---|---|---|
| $1.47 \times 10^9$ PFU/ml | $5.62 \times 10^4$ | $3.16 \times 10^1$ | 3.26 |
| $1.47 \times 10^8$ PFU/ml | | $3.16 \times 10^1$ | 3.26 |
| $1.47 \times 10^7$ PFU/ml | | $8.6 \times 10^1$ | 2.82 |
| $1.47 \times 10^6$ PFU/ml | | $5.62 \times 10^2$ | 2.00 |
| $1.47 \times 10^5$ PFU/ml | | $1.78 \times 10^3$ | 1.50 |
| $1.47 \times 10^4$ PFU/ml | | $5.62 \times 10^3$ | 1.00 |
| $1.47 \times 10^3$ PFU/ml | | $5.62 \times 10^3$ | 1.00 |

T4 bacteriophage titre inhibiting the proliferation of HAdV-5 in 50% ($IC_{50}$)=$3.83 \times 10^5$ (SD=0.456 $\log_{10}$ of the T4 titre)

B.2 HAdV-5 at a titre of 10 $TCID_{50}$, A549 line, results averaged from 12 data points.

| T4 bacteriophage titre | Control HDaV-5 titre | HDaV-5 titre in lines treated with the T4 phage | HDaV-5 titre reduction in relation to the control[log10 of the titre] |
|---|---|---|---|
| $1.47 \times 10^9$ PFU/ml | $3.16 \times 10^3$ | $1.00 \times 10^1$ | 2.50 |
| $1.47 \times 10^8$ PFU/ml | | $1.00 \times 10^1$ | 2.50 |
| $1.47 \times 10^7$ PFU/ml | | $1.00 \times 10^1$ | 2.50 |

-continued

| T4 bacteriophage titre | Control HDaV-5 titre | HDaV-5 titre in lines treated with the T4 phage | HDaV-5 titre reduction in relation to the control[log10 of the titre] |
|---|---|---|---|
| $1.47 \times 10^6$ PFU/ml | | $1.36 \times 10^1$ | 2.14 |
| $1.47 \times 10^5$ PFU/ml | | $2.30 \times 10^1$ | 1.17 |
| $1.47 \times 10^4$ PFU/ml | | $2.15 \times 10^2$ | 0.67 |
| $1.47 \times 10^3$ PFU/ml | | $6.80 \times 10^2$ | 0.17 |

T4 bacteriophage titre inhibiting the proliferation of HAdV-5 in 50% ($IC_{50}$)=$1.54 \times 10^5$ (SD=0.165 $\log_{10}$ of the T4 titre)

B.3 HAdV-5 at a titre of 100 $TCID_{50}$, HEK-293 line, results averaged from 12 data points.

| T4 bacteriophage titre | Control HDaV-5 titre | HDaV-5 titre in lines treated with the T4 phage | HDaV-5 titre reduction in relation to the control[log10 of the titre] |
|---|---|---|---|
| $1.47 \times 10^9$ PFU/ml | $1.39 \times 10^5$ | $1.39 \times 10^1$ | 4.00 |
| $1.47 \times 10^8$ PFU/ml | | $3.74 \times 10^1$ | 3.57 |
| $1.47 \times 10^7$ PFU/ml | | $4.64 \times 10^2$ | 2.48 |
| $1.47 \times 10^6$ PFU/ml | | $3.98 \times 10^3$ | 1.54 |
| $1.47 \times 10^5$ PFU/ml | | $2.19 \times 10^4$ | 0.82 |
| $1.47 \times 10^4$ PFU/ml | | $1.00 \times 10^5$ | 0.14 |
| $1.47 \times 10^3$ PFU/ml | | $1.00 \times 10^5$ | 0.14 |

T4 bacteriophage titre inhibiting the proliferation of HAdV-5 in 50% ($IC_{50}$)=$3.57 \times 10^6$ (SD=0.31 $\log_{10}$ of the T4 titre)

B.4 HAdV-5 at a titre of 10 $TCID_{50}$, HEK-293 line, results averaged from 12 data points.

| T4 bacteriophage titre | Control HDaV-5 titre | HDaV-5 titre in lines treated with the T4 phage | HDaV-5 titre reduction in relation to the control[log10 of the titre] |
|---|---|---|---|
| $1.47 \times 10^9$ PFU/ml | $1.30 \times 10^4$ | $7.20 \times 10^1$ | 2.26 |
| $1.47 \times 10^8$ PFU/ml | | $3.17 \times 10^2$ | 1.61 |
| $1.47 \times 10^7$ PFU/ml | | $1.00 \times 10^4$ | 0.11 |
| $1.47 \times 10^6$ PFU/ml | | $1.00 \times 10^4$ | 0.11 |
| $1.47 \times 10^5$ PFU/ml | | $1.00 \times 10^4$ | 0.11 |
| $1.47 \times 10^4$ PFU/ml | | $1.00 \times 10^4$ | 0.11 |
| $1.47 \times 10^3$ PFU/ml | | $1.00 \times 10^4$ | 0.11 |

T4 bacteriophage titre inhibiting the proliferation of HAdV-5 in 50% ($IC_{50}$)=$6.82 \times 10^7$ (SD=0.183 $\log_{10}$ of the T4 titre)

Figure 2:
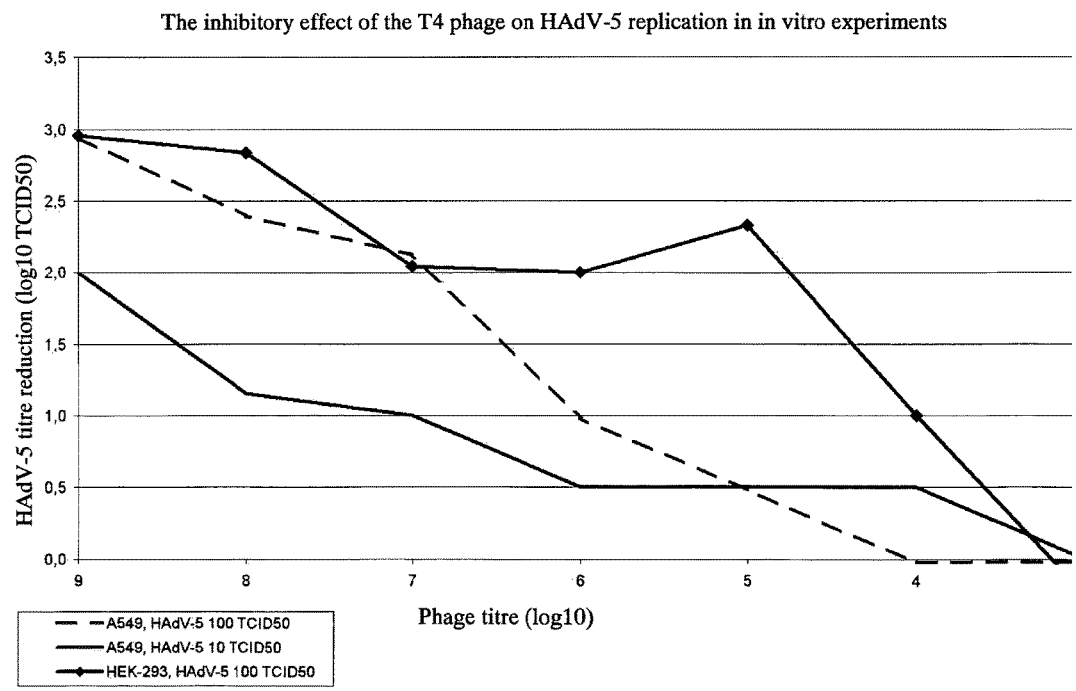
FIG. 2 shows the inhibitory effect of a preparation containing the T4 phage on the replication of HAdV-5.

C. Evaluation of the effect of the phage on the replication phase of intracellular HAdV-5—FIG. 2

C.1 HAdV-5 at a titre of 100 $TCID_{50}$, A549 line, results averaged from 12 data points.

| T4 bacteriophage titre | Control HDaV-5 titre | HDaV-5 titre in lines treated with the T4 phage | HDaV-5 titre reduction in relation to the control[log10 of the titre] |
|---|---|---|---|
| $1.47 \times 10^9$ PFU/ml | $9.49 \times 10^4$ | $1.08 \times 10^2$ | 2.94 |
| $1.47 \times 10^8$ PFU/ml | | $3.81 \times 10^2$ | 2.39 |
| $1.47 \times 10^7$ PFU/ml | | $7.06 \times 10^2$ | 2.13 |
| $1.47 \times 10^6$ PFU/ml | | $9.99 \times 10^3$ | 0.97 |
| $1.47 \times 10^5$ PFU/ml | | $3.16 \times 10^4$ | 0.48 |
| $1.47 \times 10^4$ PFU/ml | | $9.99 \times 10^4$ | 0.00 |
| $1.47 \times 10^3$ PFU/ml | | $9.99 \times 10^4$ | 0.00 |

T4 bacteriophage titre inhibiting the proliferation of HAdV-5 in 50% ($IC_{50}$)=$2.15 \times 10^6$ (SD=0.234 $\log_{10}$ of the T4 titre)

C.2 HAdV-5 at a titre of 10 $TCID_{50}$, A549 line, results averaged from 12 data points.

| T4 bacteriophage titre | Control HDaV-5 titre | HDaV-5 titre in lines treated with the T4 phage | HDaV-5 titre reduction in relation to the control[log10 of the titre] |
|---|---|---|---|
| $1.47 \times 10^9$ PFU/ml | $1.00 \times 10^4$ | $1.01 \times 10^2$ | 1.99 |
| $1.47 \times 10^8$ PFU/ml | | $7.06 \times 10^2$ | 1.15 |
| $1.47 \times 10^7$ PFU/ml | | $1.00 \times 10^3$ | 1.00 |
| $1.47 \times 10^6$ PFU/ml | | $3.16 \times 10^3$ | 0.50 |
| $1.47 \times 10^5$ PFU/ml | | $3.16 \times 10^3$ | 0.50 |
| $1.47 \times 10^4$ PFU/ml | | $3.16 \times 10^3$ | 0.50 |
| $1.47 \times 10^3$ PFU/ml | | $6.80 \times 10^2$ | 0.00 |

T4 bacteriophage titre inhibiting the proliferation of HAdV-5 in 50% ($IC_{50}$)=$8.77 \times 10^7$ (SD=0.552 $\log_{10}$ of the T4 titre)

C.3 HAdV-5 at a titre of 100 $TCID_{50}$, HEK-293 line, results averaged from 12 data points.

| T4 bacteriophage titre | Control HDaV-5 titre | HDaV-5 titre in lines treated with the T4 phage | HDaV-5 titre reduction in relation to the control[log10 of the titre] |
|---|---|---|---|
| $1.47 \times 10^9$ PFU/ml | $3.16 \times 10^4$ | $3.50 \times 10^1$ | 2.96 |
| $1.47 \times 10^8$ PFU/ml | | $4.60 \times 10^1$ | 2.84 |
| $1.47 \times 10^7$ PFU/ml | | $2.85 \times 10^2$ | 2.04 |
| $1.47 \times 10^6$ PFU/ml | | $3.16 \times 10^2$ | 2.00 |
| $1.47 \times 10^5$ PFU/ml | | $1.46 \times 10^2$ | 2.34 |
| $1.47 \times 10^4$ PFU/ml | | $3.16 \times 10^3$ | 1.00 |
| $1.47 \times 10^3$ PFU/ml | | $5.62 \times 10^4$ | 0.00 |

T4 bacteriophage titre inhibiting the proliferation of HAdV-5 in 50% ($IC_{50}$)=$1.18 \times 10^4$ (SD=0.468 $\log_{10}$ of the T4 titre)

4. Conclusions

1. We noted no cytotoxic effects of the T4 bacteriophage preparation in either of the two cell lines used: neither in the immortalised line $A_{549}$ nor in the diploid line HEK-293.

2. We determined the unequivocal effect of T4 bacteriophages on the level of HAdV-5 proliferation in both tested cell lines, in experiments for determining the effect of bacteriophages both on adsorption, as well as on HAdV replication. The observed infective titre reduction in quantities corresponding to $IC_{50}$ was from 1.10 do 2.34 log 10 of the HAdV-5 titre.

3. The most pronounced inhibitory effect on the adsorption of type 5 adenoviruses was observed in the $A_{549}$ line for both studied virus titres (100 and 10 $TCID_{50}$). The $IC_{50}$ values for the bacteriophages were $3.83 \times 10^5$ and $1.54 \times 10^5$ PFU/ml respectively.

4. In the experimental variant relating to the evaluation of the effect of T4 bacteriophages on HAdV-5 replication, the most significant effect was observed in the HEK-293 cell line infected with HAdV-5 at a titre of 100 $TCID_{50}$. The bacteriophage $IC_{50}$ value was $1.18 \times 10^4$ PFU/ml.

The invention claimed is:
1. A method for improving the state of health of patients infected with adenovirus HadV-5, comprising providing a T4 phage preparation comprising an effective amounts of T4 phage to inhibit the proliferation of adenovirus HadV-5 by

50%, and administering the preparation to the patients in need thereof, wherein the T4 phage titers in said preparation range from about $1.47 \times 10^9$ to $1.47 \times 10^3$ PFU/ml.

2. A method of treating a HadV-5 adenoviral infection in a mammal in need thereof comprising administering to said mammal an effective amount of a preparation comprising T4 bacteriophage strain.

3. The method of claim 2, wherein the T4 phage titers range from about $1.47 \times 10^9$ to $1.47 \times 10^3$ PFU/ml.

* * * * *